(12) United States Patent
Klostermeyer et al.

(10) Patent No.: US 6,200,306 B1
(45) Date of Patent: Mar. 13, 2001

(54) BEND CLIP FOR FLEXIBLE ROTATOR

(75) Inventors: Tammi E. Klostermeyer; Christopher Heinrich, both of Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/320,119

(22) Filed: May 26, 1999

(51) Int. Cl.[7] .................................................. A61B 17/00
(52) U.S. Cl. ............................ 606/1; 600/146; 600/143; 600/144; 604/524; 604/530; 604/532
(58) Field of Search ................................ 600/146, 143, 600/144; 606/1; 604/524, 530, 532

(56) References Cited

U.S. PATENT DOCUMENTS

| | | | |
|---|---|---|---|
| 5,255,668 | * 10/1993 | Umeda | 128/4 |
| 5,582,607 | 12/1996 | Lackman | 606/1 |
| 5,749,828 | * 5/1998 | Solomon et al. | 600/141 |
| 5,772,655 | * 6/1998 | Bauer et al. | 606/1 |
| 5,873,817 | * 2/1999 | Kokish et al. | 600/143 |
| 5,941,818 | * 8/1999 | Hori et al. | 600/143 |
| 5,976,075 | * 11/1999 | Beane et al. | 600/146 |
| 6,004,329 | * 12/1999 | Myers et al. | 606/108 |

* cited by examiner

*Primary Examiner*—Linda C. M. Dvorak
*Assistant Examiner*—Jocelyn Ram
(74) *Attorney, Agent, or Firm*—Timothy L. Scott; Philip S. Lyren

(57) ABSTRACT

A pusher-rotator for installing a heart valve prosthesis including a handle and a flexible shaft extending from the handle. A valve holder is attached to a terminal end of the shaft. A bendable member is formed of a material which is bendable to hold a fixed shape. The bendable member includes multiple contact points for supporting the flexible shaft at spaced apart support points and maintaining the flexible shaft rotatable in a flexed orientation.

25 Claims, 5 Drawing Sheets

BEND CLIP FOR FLEXIBLE ROTATOR

BACKGROUND

The disclosures herein relate generally to a holder for a prosthetic heart valve and more particularly to a clip for maintaining a bent position in the shaft portion of the holder.

When attaching a universal mechanical heart valve during a surgical procedure, a surgeon does not directly handle the valve, thereby maintaining the valve sterile and avoiding possible damage to the valve. Typically a valve holder is coupled with a flexible pusher-rotator handle. The valve holder is attached to the valve. The handle permits the surgeon to push and rotate the valve into the natural heart valve annulus for final suturing.

The handle and valve holder must allow the surgeon to position the valve and sewing cuff in the natural heart valve annulus by manually applied axial and rotational movement of the flexible handle. Current handles incorporate a flexible shaft formed of a super elastic material such as the product sold under the name Nitinol. As such the shaft can be flexed and rotated in a flexed position to facilitate proper placement of the mechanical valve in the natural valve annulus. Current flexible shafts can require two points of contact (hand positions) in some situations in order to properly flex the shaft into position and rotate the valve and valve holder into the annulus. One of the points of contact is on the handle and the other point of contact is on the shaft near the valve holder. This is especially the case when operating on the mitral valve, where getting a hand on the shaft close to the valve holder, is difficult due to space limitations. Trying to manipulate the valve holder at the end of the flexible shaft with another instrument, positioned near the valve holder, is difficult due to the size and flexibility of the shaft. Therefore, attempting to bend the flexible device to seat the mechanical valve is difficult.

In addition, when the flexible shaft is in a bent position, there is a possibility that the valve holder end of the shaft could spring-back to the natural straight configuration when the holder is disengaged from the mechanical valve. This, or an unexpected spring-back action, would be undesirable.

An example of a flexible shaft device is described in U.S. Pat. No. 5,582,607 which discloses a heart valve prosthesis rotator which also has an annealed stainless steel shaft which can be bent by the surgeon interoperatively. The shaft will retain its shape after bending. Surrounding the shaft is a drive coil which connects a rotator head at a proximal end of the shaft to a drive knob at a distal end of the shaft and adjacent a handle. By turning the drive knob, a surgeon can turn the rotator head, thus orienting the prosthetic heart valve. Torsional motion is carried along the path defined by the bendable shaft so that the rotator head can be turned without displacing the handle of the heart valve rotator.

Therefore, what is needed is a device which avoids the need for a two-point contact in order to bend and hold the flexible shaft of a pusher rotator and which avoids the possibility of shaft spring-back either inadvertently or when the valve holder is disengaged from the mechanical valve.

SUMMARY

One embodiment, accordingly, provides a bendable component which can hold a shape and can maintain that shape while attached to a flexible shaft which is rotatable in the component. To this end, a bend clip for a flexible pusher-rotator includes a bendable member formed of a material which is bendable to hold a fixed shape. The bendable member includes multiple contact points for supporting a flexible shaft at spaced apart support points and maintaining the flexible shaft rotatable in a flexed position.

A principal advantage of this embodiment is that the bend clip avoids the need for a two-point hand contact in order to bend and hold the flexible shaft of a pusher-rotator, and avoids a possible spring back of the shaft either inadvertently or when a valve holder at a terminal end of the shaft is disengaged from a mechanical valve being installed.

BRIEF DESCRIPTION OF THE DRAWING FIGURES

DETAILED DESCRIPTION

Figure 1:
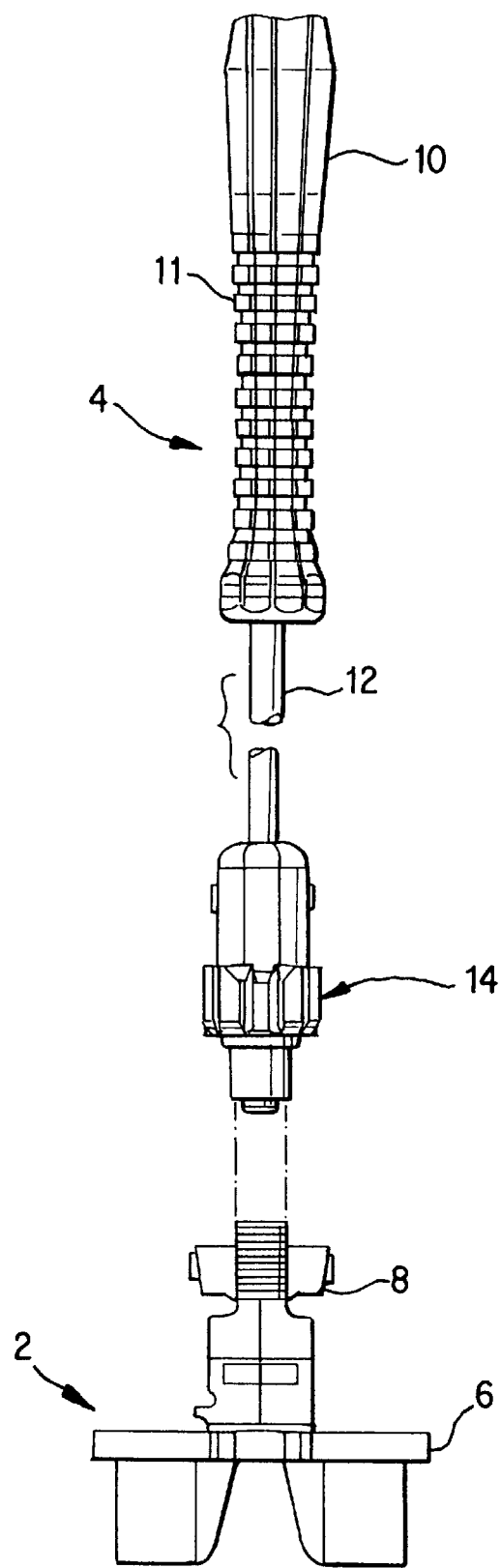
FIG. 1 is an exploded view illustrating an embodiment of a pusher-rotator assembly.

As shown in FIG. 1, a prosthetic heart valve holder 2 is provided to be releasably coupled with a pusher-rotator assembly 4 for engaging and installing a heart valve prosthesis. Valve holder 2 includes a valve coupling member 6 and a handle receiving member 8. Pusher-rotator assembly 4 includes a handle or grasping end 10, a flexible medial shaft segment 12, and a coupling assembly 14 attached to a terminal end of shaft 12.

Pusher-rotator 4 is made from biocompatible, repeatedly sterilizable materials; preferably, grasping end 10 and coupling assembly 14 are made from polysulfone and shaft 12 is preferably made of a super elastic material sold under the name Nitinol. Grasping end 10 includes a ribbed or textured outer surface 11. Also, grasping end 10 may be tapered or otherwise formed to provide a more ergonomic grasping area. Shaft 12 is generally annular in cross section and made from super flexible material which allow a surgeon to bend grasping end 10 relative to coupling assembly 14 during implantation. Consequently, the surgeon has greater flexibility in positioning the prosthetic valve while obtaining a desired view of the implantation area.

A bend clip is provided for use with pusher-rotator assembly 4. In one embodiment, FIG. 2, a bend clip 20 includes a first end 22 and a second end 24. Bend clip 20 is formed of a material such as stainless steel which is bendable to hold a fixed shape, FIG. 2A. Bend clip 20, FIGS. 2 and 2A, includes a bendable member in the form of an elongated tube 26 having a full-length aperture 28 extending from first end 22 to second end 24 for receiving shaft 12.

Figure 3:
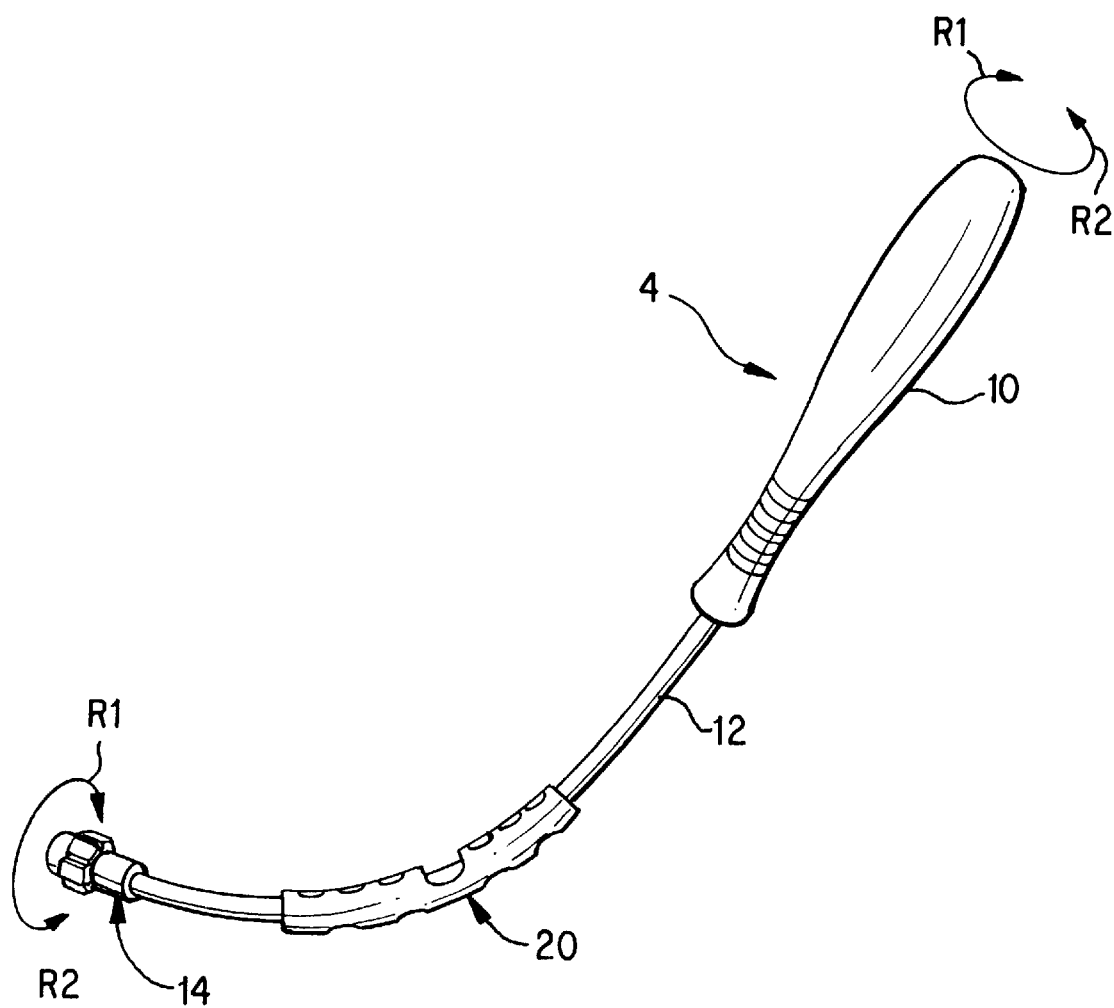
FIG. 3 is an isometric view illustrating an embodiment of a pusher-rotator assembly having a shaft held in a bent position by a bend clip.

Tube 26 has an outer annular wall 30 including a plurality of apertures 32 formed therein for facilitating the cleaning of bend clip 20 which may be mounted for axial movement on shaft 12. A slot 34 is formed in a portion of annular peripheral wall 30 to provide a relief for bending tube 26. The bendable tube 26 includes multiple contact points throughout aperture 28 for supporting flexible shaft 12 at spaced apart support points, such as at ends 22 and 24, so that flexible shaft 12 is maintained rotatable and slidable while flexed within aperture 28 when tube 26 is holding a bend shape, see FIG. 3. In this manner, a prosthetic valve (not shown) may be positioned according to the bend of bend clip 20 so that rotation of grasping end 10 of pusher-rotator 4, in directions indicated at R1 and R2, will similarly rotate coupling assembly 14 via shaft 12 rotating within bend clip 20.

Figure 4:
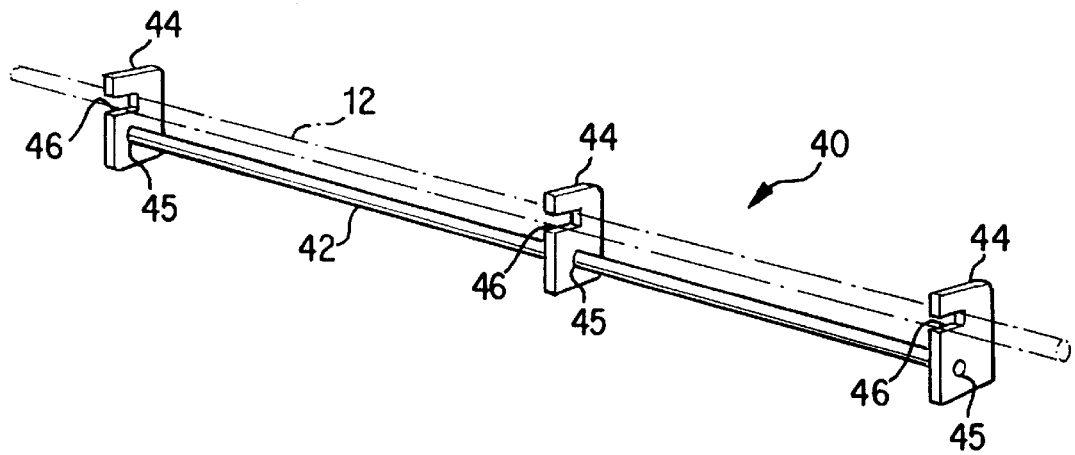
FIG. 4 is an isometric view illustrating another embodiment of a bend clip supporting a shaft in a straight position.
Figure 4A:
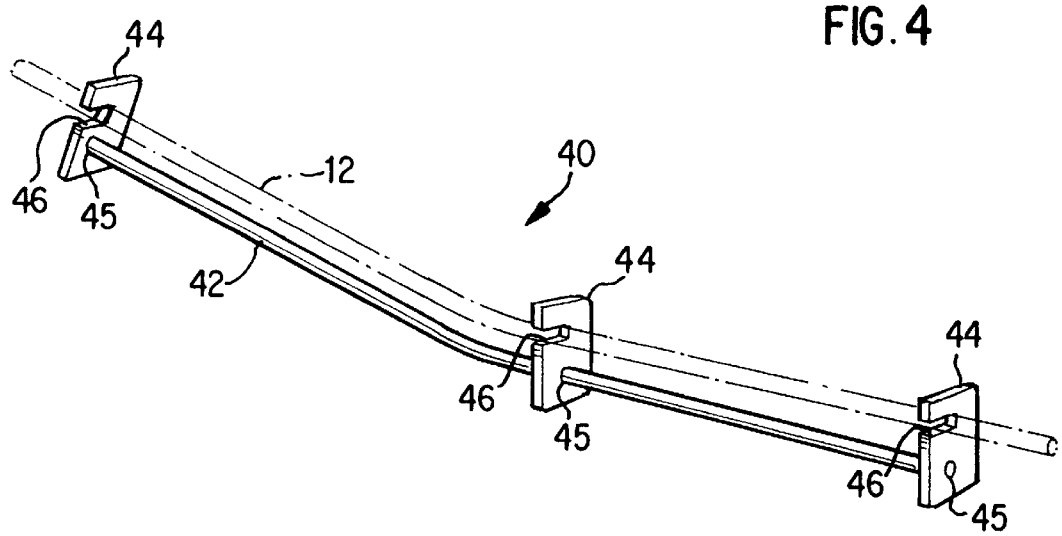
FIG. 4A is an isometric view illustrating an embodiment of a bend clip supporting a shaft in a bent position.
Figure 4B:
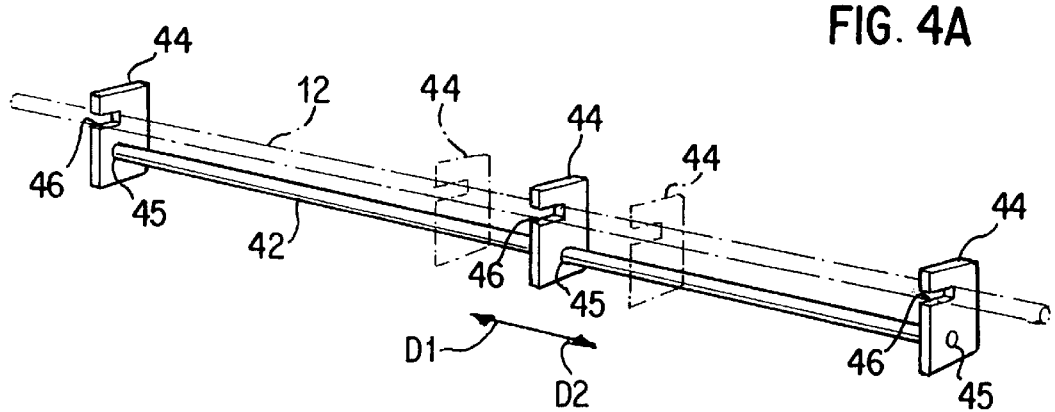
FIG. 4B is an isometric view illustrating an embodiment of a bend clip having an adjustable shaft clip.

In another embodiment, FIG. 4, a bend clip 40 includes a bendable member in the form of an elongated wire member 42 formed of a material such as stainless steel which is bendable to hold a fixed shape, FIG. 4A. Wire member 42, FIGS. 4 and 4A, includes a plurality of shaft clips 44 mounted thereon at a connection 45. Each shaft clip 44 includes a slot 46 formed therein for supporting shaft 12, which is rotatably and axially movable in each slot 46. Shaft clips 44 may be fixedly mounted on wire member 42 or, alternatively, at least one of the shaft clips may be adjustably mounted on wire member 42, see FIG. 4B, for movement in either of the directions designated D1 and D2. The bendable wire member 42 includes multiple contact points at each slot 46 for supporting shaft 12 at spaced apart support points, so that flexible shaft 12 is maintained rotatable while flexed within slots 46 when wire member 42 is holding a bend shape, see FIG. 4A.

Figure 5:
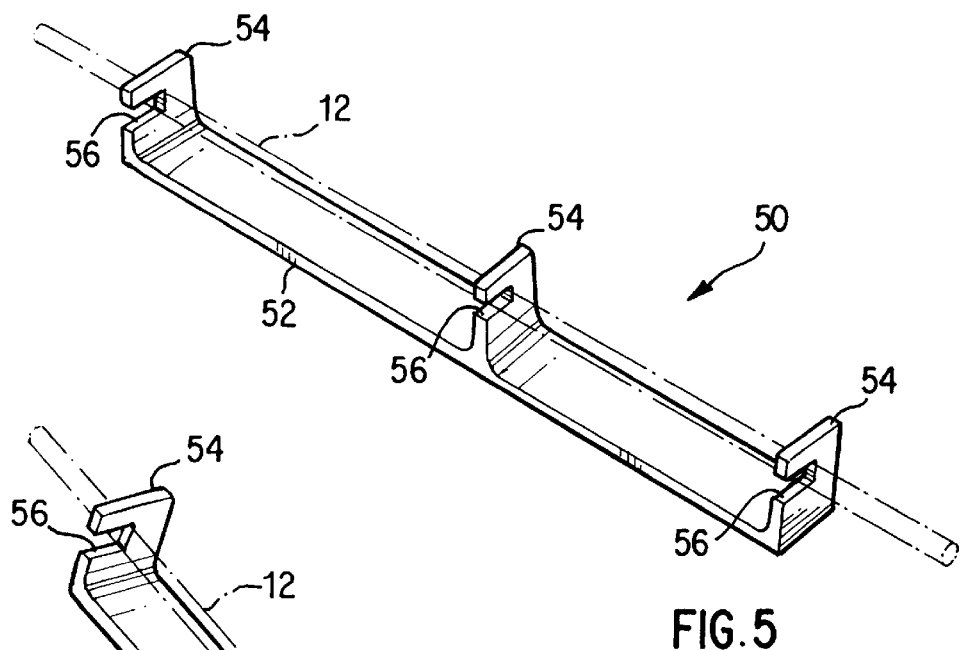
FIG. 5 is an isometric view illustrating a further embodiment of a bend clip supporting a shaft in a straight position.
Figure 5A:
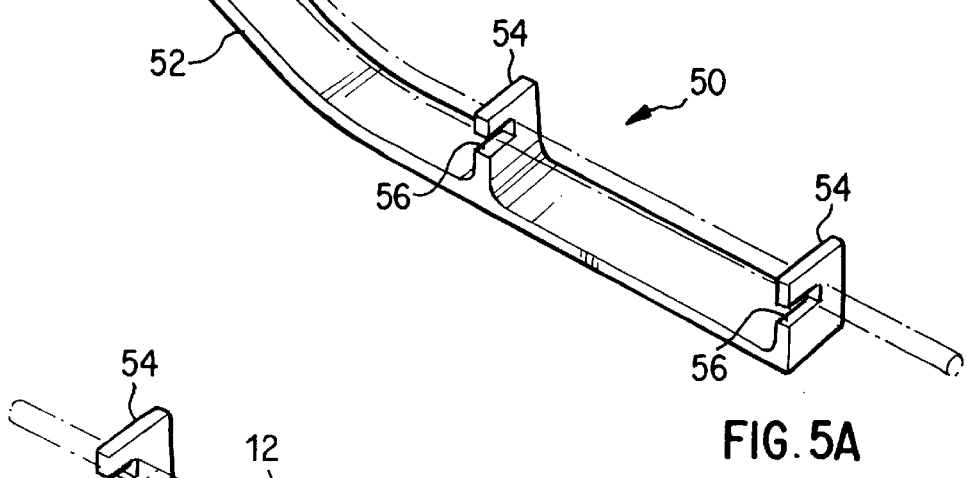
FIG. 5A is an isometric view illustrating an embodiment of a bend clip supporting a shaft in a bent position.
Figure 5B:
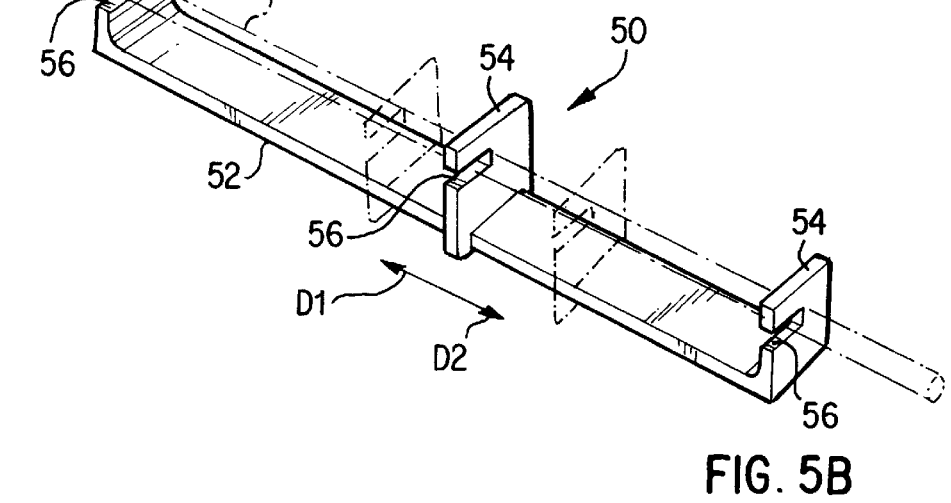
FIG. 5B is an isometric view illustrating an embodiment of a bend clip having an adjustable shaft tab.

In a further embodiment, FIG. 5, a bend clip 50 includes a bendable member in the form of an elongated bracket member 52 formed of a material such as stainless steel which is bendable to hold a fixed shape, FIG. 5A. Bracket member 52, FIGS. 5 and 5A, includes a plurality of shaft tabs 54 mounted thereon. Each shaft tab 54 includes a slot 56 formed therein for supporting shaft 12, which is rotatably and axially movable in each slot 56. Shaft tabs 54 may be fixedly mounted on bracket member 52 or, alternatively, at least one of the shaft clips may be adjustably mounted on bracket member 52, see FIG. 5B, for movement in either of the directions designated D1 and D2. The bendable bracket member 52 includes multiple contact points at each slot 56 for supporting shaft 12 at spaced apart support points, so that flexible shaft 12 is maintained rotatable while flexed within slots 56 when bracket member 52 is holding a bend shape, see FIG. 5A.

Figure 2:
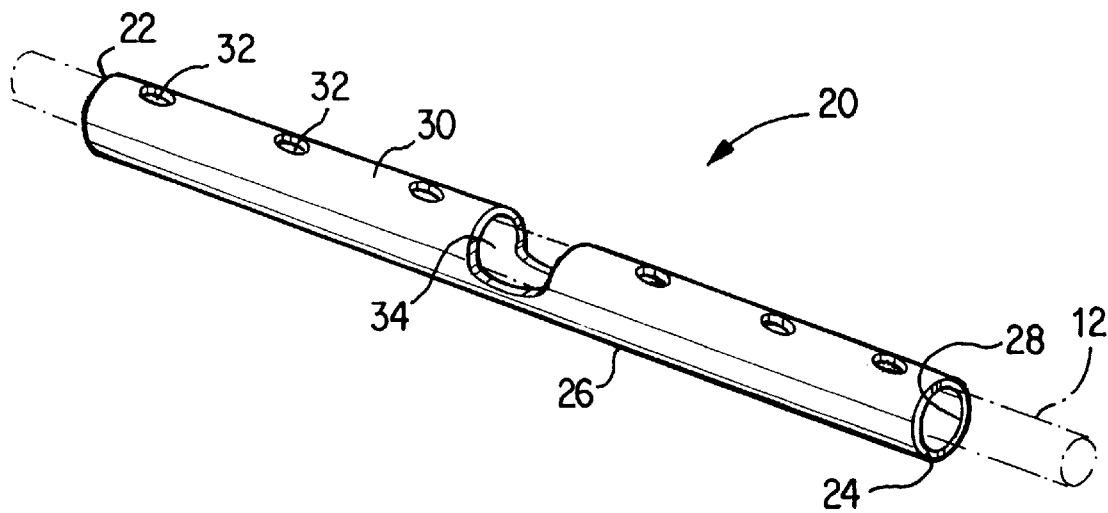
FIG. 2 is an isometric view illustrating an embodiment of a bend clip supporting a shaft in a straight position.
Figure 2A:
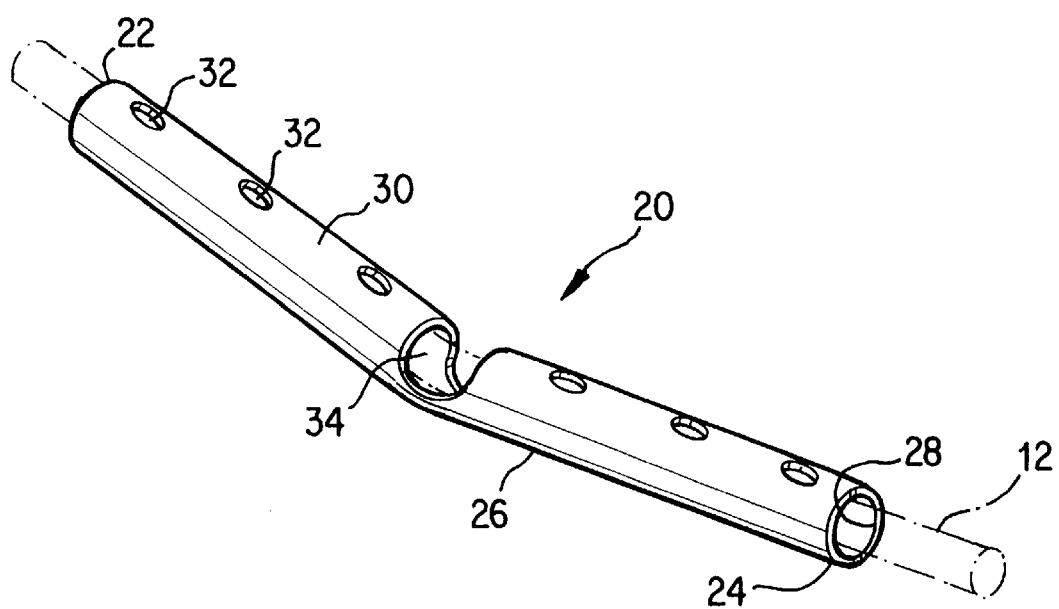
FIG. 2A is an isometric view illustrating an embodiment of a bend clip supporting a shaft in a bent position.

In operation a bend clip includes an aperture for receiving shaft 12, FIG. 2, or may be a clip-on attachment to shaft 12 via slotted shaft clips, FIG. 4, or slotted shaft tabs, FIG. 5. The bend clip may be bent to hold a flexed orientation in shaft 12 which closely approximates a bend angle desired to enable the surgeon to position a heart valve prosthesis adjacent a natural heart annulus, and then push and rotate the valve into position for attachment to the annulus. The shaft 12 is supported by the bend clip for rotation in the flexed orientation.

As a result, one embodiment provides a bend clip for a flexible pusher-rotator including a bendable member formed of a material which is bendable to hold a fixed shape. The bendable member includes multiple contact points for supporting a flexible shaft at spaced apart support points and maintaining the flexible shaft rotatable in a flexed orientation.

Another embodiment provides a pusher-rotator for installing a heart valve prosthesis including a handle and a flexible shaft extending from the handle. A valve holder is attached to a terminal end of the shaft. A bendable member is formed of a material which is bendable to hold a fixed shape. The bendable member includes multiple contact points for supporting the flexible shaft at spaced apart support points and maintaining the flexible shaft rotatable in a flexed orientation.

A further embodiment provides a method of maintaining a flexible pusher-rotator shaft in a flexed orientation. A bendable member is formed of a material which is bendable to hold a fixed shape. Multiple, spaced apart support points are formed on the bendable member. The bendable member is then mounted on a flexible shaft so that the bendable member supports the flexible shaft at the spaced apart support points along the shaft for maintaining the shaft in a rotatable flexed orientation.

As it can be seen, the principal advantages of these embodiments are that the bend clip avoids the need for a two-point hand contact in order to bend and hold the flexible shaft of a pusher-rotator, and avoids a possible spring back of the shaft either inadvertently or when a valve holder at a terminal end of the shaft is disengaged from a mechanical valve being installed. The clip allows a surgeon to bend the device to a desired position. The clip device then maintains the bend configuration and allows the shaft to rotate freely. The clip device may be a permanent component of the pusher-rotator or may be removably attached as a clip-on component of the pusher-rotator. The permanent component configuration comprises a tube with a plurality of holes formed therein for easy cleaning.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A bend clip for a flexible pusher-rotator comprising:
   a bendable member including a first end and a second end, the bendable member being formed of a material which is bendable to hold a fixed bent shape; and
   the bendable member including multiple contact points for supporting a flexible shaft at spaced apart support points and maintaining the flexible shaft rotatable in a flexed orientation.

2. The bend clip as defined in claim 1 wherein the bendable member includes an elongated tube member including a full length aperture formed therethrough from the first end to the second end.

3. The bend clip as defined in claim 2 wherein the tube member includes an annular peripheral wall having a plurality of apertures formed therethrough.

4. The bend clip as defined in claim 3 wherein the tube member includes a slot formed in a portion of the annular peripheral wall between the first end and the second end.

5. The bend clip as defined in claim 1 wherein the bendable member includes an elongated wire member having a plurality of shaft clips mounted thereon.

6. The bend clip as defined in claim 5 wherein each shaft clip includes a shaft retaining slot formed therein.

7. The bend clip as defined in claim 6 wherein at least one shaft clip is movably mounted on the elongated wire member.

8. The bend clip as defined in claim 6 wherein each shaft clip is fixedly mounted on the elongated wire member.

9. The bend clip as defined in claim 1 wherein the bendable member includes an elongated bracket member having a plurality of shaft tabs mounted thereon.

10. The bend clip as defined in claim 9 wherein each shaft tab includes a shaft retaining slot formed therein.

11. The bend clip as defined in claim 10 wherein at least one shaft tab is movably mounted on the elongated bracket member.

12. The bend clip as defined in claim 10 wherein each shaft tab is fixedly mounted on the elongated bracket member.

13. A pusher-rotator for installing a heart valve prosthesis comprising:
   a handle;
   a flexible shaft extending from the handle;
   a valve holder attached to a terminal end of the shaft;
   a bendable member mounted on the shaft, the bendable member including a first end and a second end and being formed of a material which is bendable to hold a fixed bent shape; and
   the bendable member including multiple contact points for supporting the flexible shaft at spaced apart support points and maintaining the flexible shaft rotatable in a flexed orientation.

14. The pusher-rotator as defined in claim 13 wherein the bendable member includes an elongated tube member including a full length aperture formed therethrough from the first end to the second end.

15. The pusher-rotator as defined in claim 14 wherein the tube member includes an annular peripheral wall having a plurality of apertures formed therethrough.

16. The pusher-rotator as defined in claim 15 wherein the tube member includes a slot formed in a portion of the annular peripheral wall between the first end and the second end.

17. The pusher-rotator as defined in claim 13 wherein the bendable member includes an elongated wire member having a plurality of shaft clips mounted thereon.

18. The pusher-rotator as defined in claim 17 wherein each shaft clip includes a shaft retaining slot formed therein.

19. The pusher-rotator as defined in claim 18 wherein at least one shaft clip is movably mounted on the elongated wire member.

20. The pusher-rotator as defined in claim 18 wherein each shaft clip is fixedly mounted on the elongated wire member.

21. The pusher-rotator as defined in claim 13 wherein the bendable member includes an elongated bracket member having a plurality of shaft tabs mounted thereon.

22. The pusher-rotator as defined in claim 21 wherein each shaft tab includes a shaft retaining slot formed therein.

23. The pusher-rotator as defined in claim 22 wherein at least one shaft tab is movably mounted on the elongated bracket member.

24. The pusher-rotator as defined in claim 22 wherein each shaft tab is fixedly mounted on the elongated bracket member.

25. A method of maintaining a flexible pusher-rotator shaft in a flexed orientation comprising the steps of:
   forming a bendable member of a material which is bendable to hold a fixed shape;
   forming multiple spaced apart support points on the bendable member;
   mounting the bendable member on a flexible shaft so that the bendable member supports the flexible shaft at the spaced apart support points along the shaft; and
   maintaining the shaft in a rotatable flexed orientation.

* * * * *